US008761904B2

(12) United States Patent
Chambers

(10) Patent No.: US 8,761,904 B2
(45) Date of Patent: Jun. 24, 2014

(54) COCHLEAR IMPLANT WITH MODIFIED INTRACOCHLEAR ELECTRODE MEMBER

(75) Inventor: John Chambers, Mona Vale (AU)

(73) Assignee: Cochlear Limited, Macquarie University NSW (AU)

( * ) Notice: Subject to any disclaimer, the term of this patent is extended or adjusted under 35 U.S.C. 154(b) by 298 days.

(21) Appl. No.: 13/003,572

(22) PCT Filed: Jul. 2, 2009

(86) PCT No.: PCT/AU2009/000851
§ 371 (c)(1),
(2), (4) Date: Apr. 1, 2011

(87) PCT Pub. No.: WO2010/003173
PCT Pub. Date: Jan. 14, 2010

(65) Prior Publication Data
US 2011/0178587 A1    Jul. 21, 2011

(30) Foreign Application Priority Data
Jul. 10, 2008    (AU) .................................. 2008903558

(51) Int. Cl.
*A61N 1/04*    (2006.01)
(52) U.S. Cl.
USPC ........................................... 607/137; 607/57

(58) Field of Classification Search
USPC ................................................. 607/55–57, 137
See application file for complete search history.

(56) References Cited

U.S. PATENT DOCUMENTS

| 6,116,413 | A | 9/2000 | Tabor et al. |
|---|---|---|---|
| 7,146,227 | B2 | 12/2006 | Dadd et al. |
| 2003/0167077 | A1* | 9/2003 | Blamey et al. .................. 607/57 |
| 2006/0004432 | A1 | 1/2006 | Parker et al. |
| 2006/0287689 | A1 | 12/2006 | Debruyne et al. |

FOREIGN PATENT DOCUMENTS

WO    WO-03049658    6/2003

OTHER PUBLICATIONS

International Search Report for PCT/AU2009/000851, mailed Sep. 21, 2009, 5 pages.
Written Opinion for PCT/AU2009/000851, mailed Sep. 21, 2009, 7 pages.

* cited by examiner

*Primary Examiner* — Allen Porter, Jr.
(74) *Attorney, Agent, or Firm* — K&L Gates, LLP

(57) ABSTRACT

An implantable tissue stimulating electrode device comprising: a carrier member; one or more biocompatible electrodes positioned on the carrier member, said electrodes having a surface; and an ionically conductive layer disposed at least over a portion of the surface of one or more electrodes.

21 Claims, 2 Drawing Sheets

COCHLEAR IMPLANT WITH MODIFIED INTRACOCHLEAR ELECTRODE MEMBER

CROSS-REFERENCE TO RELATED APPLICATION

The present application is a National Stage application of International Patent Application No. PCT/AU2009/000851, filed Jul. 2, 2009, and claims priority from Australian Patent Application No. 2008903558, filed Jul. 10, 2008. The content of these applications is hereby incorporated by reference herein.

BACKGROUND

1. Field of the Invention

The present invention relates to devices that deliver neural stimulation to the body, such as cochlear implants.

2. Related Art

Cochlear implant hearing prostheses are a well-recognized therapeutic means of restoring a sense of hearing for profoundly deaf persons. Using one or more microphones to convert incoming sound into electrical signals, these prostheses process the amplitude and frequency information contained within these signals to create several discrete channels of electro-neural stimulation for delivery to the human organ of hearing called the cochlear.

Since the hearing cells targeted by these prostheses are spatially distributed along the spiral pathways of the human cochlea, electrical stimulation intended to evoke perceptions of both the amplitude and frequency of incoming sound must be distributed spatially in a likewise fashion. As a consequence, each stimulation channel is thus assigned to deliver electrical stimulation in response to a particular range of incoming sound frequencies.

While thousands to perhaps millions of frequency distinguishing neural cells are implicated in normal hearing, current art electro-stimulation hearing prostheses are constrained by size and other factors to deliver only twenty or so discrete channels of stimulation. This number is sufficient to allow for speech recognition and conversation in quiet environments, but makes it difficult for speech to be easily discernible when background noise levels increase.

Users of languages predominantly more tonal than English are especially challenged since the limited number discrete channels of stimulation cannot replicate the inflection of a word to distinguish its meaning. It is also an unfortunate fact that while many users of current art devices report some enjoyment of musical sounds, tonal appreciation of even the simplest of tunes is beyond them as there are simply not enough stimulation channels available to fully restore the sense of hearing.

This limitation arises from the need to deliver a time constrained, minimum level of electric charge in order to evoke a hearing-like sensation with a particular apparent loudness or intensity. Current art electrodes are already close to the minimum size necessary to prevent non-reversible galvanic reactions, electrode corrosion, and the creation of chemical species that can destroy the viability of the sensory cells targeted by the delivered stimulation. These reactions increasingly occur as the electrode to body tissue interface impedance, and hence the voltage developed during the application of stimulation current, rises as the surface area of the electrode is reduced.

Since the avoidance of such reactions is crucial to the long-term success of these prostheses, current art intra-cochlear electrodes are required to be of a particular size so as to have an outer area of at least approximately 1 square millimeter. As a consequence, in addition to limiting the total number of stimulating electrodes that can be accommodated within the cochlear, the size of the electrode also limits the depth to which the intra-cochlear electrode array can be inserted within the cochlear and the degree to which low frequency hearing can be restored, since this where the neural cells associated with low frequency perception are located.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

According to a first aspect of the present invention, an, implantable tissue stimulating electrode device is disclosed. The electrode device comprises:

a carrier member;

one or more biocompatible electrodes positioned on the carrier member, said electrodes having a surface; and an ionically conductive layer disposed at least over a portion of said surface of said one or more electrodes.

BRIEF DESCRIPTION OF THE DRAWINGS

By way of example only, embodiments of the invention are now described with reference to the accompanying drawings, in which.

DETAILED DESCRIPTION

The depicted embodiments of the present invention are shown as part of a cochlear implant system. It is to be understood that the present invention has application to other implantable prostheses including but not limited to auditory prostheses.

Figure 1:
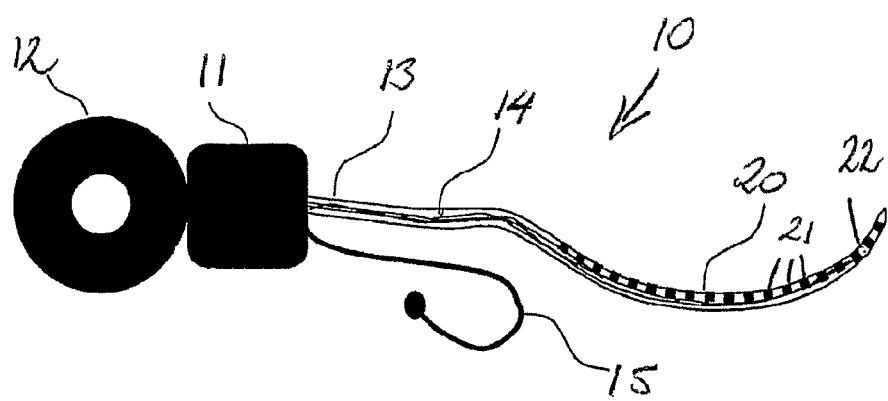
FIG. 1 depicts the principal parts of the implantable component of a cochlear implant system.

One example of an implantable component of a cochlear implant system that can use the electrode member of the present invention is depicted generally as 10 in FIG. 1. The component 10 has a hermetically sealed and biocompatible titanium housing 11 that contains a receiver/stimulator unit. This unit receives signals transmitted from an external component using a radio frequency (RF) transcutaneous magnetic induction link. Antenna coil 12 comprises the implanted part of such a link.

Extending from the housing 11 via a feedthrough is a cable 13 that extends to an implantable tissue stimulating intracochlear electrode array 20. It will be noted that a series of wires 14 extend through the cable 13 to a plurality of biocompatible electrodes 21 making up the array 20. Not all of the wires 14 are depicted for reasons of clarity. The component 10 is also shown with an optional reference electrode 15 that can be placed externally or internally of the cochlea.

Figure 2:
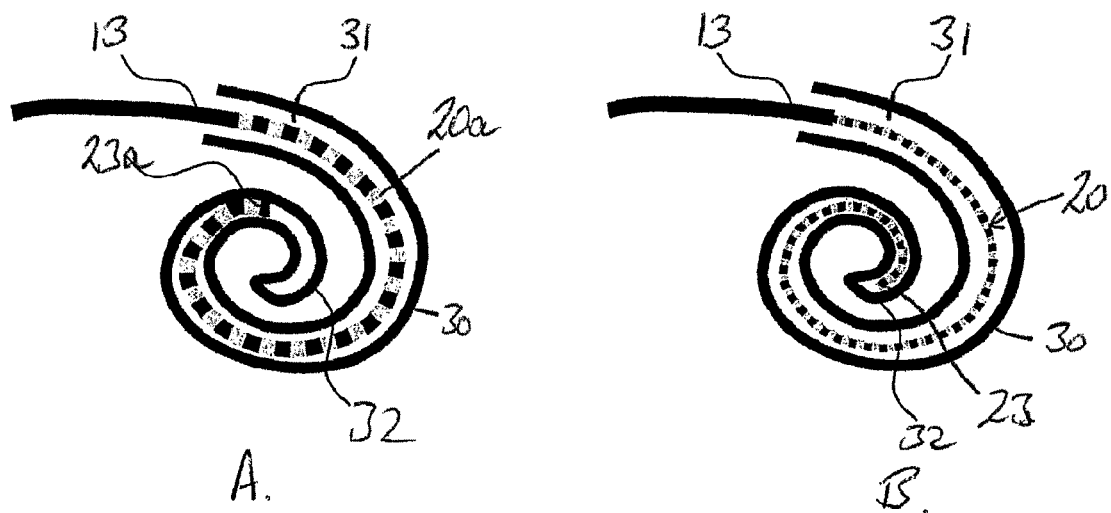
FIG. 2A is an enlarged simplified view of a prior art intra-cochlear electrode array positioned in a cochlea.
FIG. 2B is an enlarged simplified view of one embodiment of an intracochlear electrode array according to the present invention positioned in a cochlea.

The depicted embodiment of the electrode array 20 comprises a carrier member 22 and a plurality of the electrodes 21. It will be appreciated that a single electrode or less than or more than the number of electrodes depicted in the drawings could be mounted on the carrier member 22. As described below, an ionically conductive layer 40 is also disposed at least over the electrodes 21. As depicted in FIG. 2B, the electrode array 20 is designed to be inserted into the scala tympani 31 of the cochlea 30 of an implantee. Due to its construction, the electrode array 20 can be inserted relatively further into the scala tympani 31 than that is safely possible using current typical electrode arrays (depicted as 20a in FIG. 2A). It will be noted that the leading end 23a of the array 20a does not reach as close to the end 32 of the scala tympani as is achieved by the leading end 23 of the array 20 depicted in FIG. 2B.

Figure 4:
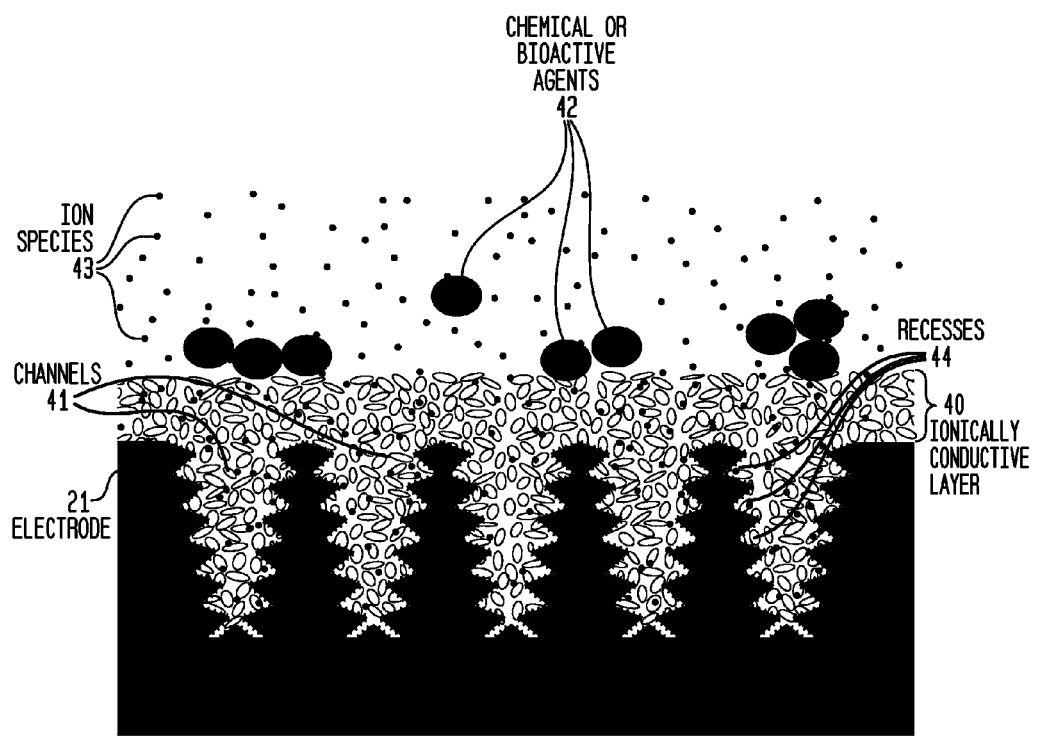
FIG. 4 is a still further enlarged cross-sectional view of one electrode of the intracochlear electrode array according to the present invention.

As shown in FIG. 4 the ionically conductive layer 40 can comprise any material that has a structure that allows conduction of ion species 43 through the layer to a surface of the electrode 21. At the same time, the layer 40 preferably has a structure that partially, substantially or wholly prevents tissue growth over the electrode 21, following implantation.

The ionically conductive layer 40 should be biocompatible, dimensionally stable, compliant, and/or capable of remaining in contact with at least a surface of the electrode 21 and, if required, the material of the carrier member 22. It can comprise a polymeric material. In one embodiment, the layer 40 can comprise an ionically conductive elastomer or a hydrogel. The hydrogel can undergo hydration prior to implantation and/or be hydrated by exposure to bodily fluids on implantation.

The hydrogel making up the ionically conductive layer 40 can be formed from polyacrylic acids, poly(meth)acrylic acids, polyalkylene oxides, polyvinyl alcohols, poly(N-vinyl lactams), polyacrylamides, poly(meth) acrylamides, or pressure sensitive adhesives such as a N-vinyl-pyrrolidone/acrylic acid copolymer.

The ionically conductive layer 40 can be further disposed over some, the majority or all of the carrier member 22. The layer 40 can further act as a lubricant and serve to assist in placement of the electrode array 20 in a desired location within an implantee.

The ionically conductive layer 40 can serve to host and release, when appropriate, beneficial chemical and/or bioactive agents 42 at the site of implantation of the electrode array 20. For example, anti-inflammatory, anti-bacterial, and/or anti-viral agents could be released from the layer 40. In another embodiment, cellular growth factors could be released from the layer 40.

The electrodes 21 are formed from a metal or alloy. In the depicted embodiment, the electrodes 21 are platinum rings.

Figure 3:
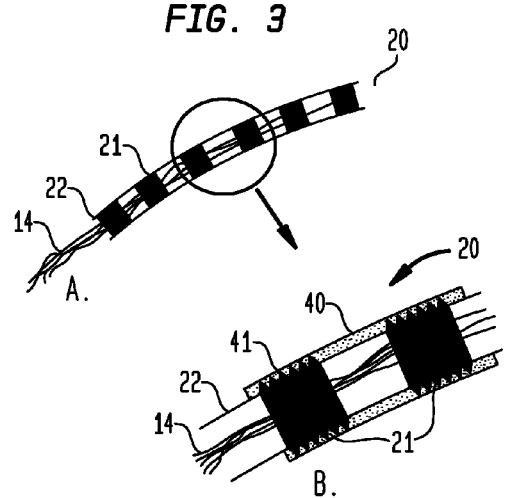
FIGS. 3A and 3B depicts two enlarged views of the intra-cochlear electrode array according to the present invention.

As depicted in FIG. 3B, the electrodes 21 are chemically etched or otherwise have undergone surface modification so as to increase the surface area of the electrode 21 than would otherwise be the case. As depicted in both FIG. 3B and FIG. 4, one or more channels 41 can be formed in the electrode 21.

As shown in FIG. 4, the presence of the channels 41 results in the ionically conductive layer 40 when applied to the electrode 21 moving relatively down and into the channels 41. The channels 41 can be substantially shaped in the form of grooves extending substantially perpendicularly with respect to the carrier member 22. As depicted in FIG. 4, the channels 41 can include recesses 44 extending substantially perpendicularly with respect to the channels 41 (i.e., substantially parallel to the carrier member 22). If a hydrogel, hydration of the layer 40 following disposition in the channels 41 serves to mechanically entrap the hydrogel layer 40 in the channels 41 and on the surface of the electrode 21. This serves to create a relatively more intimate contact between the electrode 21 and the hydrogel 40 so ensuring a relatively low impedance ionic interface between the electrode 21 and the hydrogel 40.

The carrier member 22 can be formed of a silicone elastomeric material, such as a Silastic material. The carrier member 22 preferentially adopts a spirally curved configuration but can be straightened or be straight prior to implantation.

The carrier member can have at least 22 electrodes. However, as depicted in FIG. 2B, it is envisaged that significantly more electrodes 21 can be disposed on the carrier member 22 in the present invention. Each electrode 21 can have an outer area of less than 1 mm$^2$.

The use of the ionically conductive layer 40 of the present invention provides for an electrode array 20 having relatively smaller electrodes 21 than hitherto usually used without suffering the disadvantage of undesirably increased interface impedance. The layer 40 also serves to prevent undesirable in-growth tissue over the electrodes 21 following the implantation. The relative decrease in the size of the electrodes 21 allows for manufacture of a relatively narrower carrier member 22 and potentially an increase in the number of electrodes 21 on the carrier member 22. An increase in the number of electrodes 21 will potentially allow for improvement in the quality of the sound perception delivered to an implantee, particularly when listening to music. A relatively narrow carrier member 22 also provides the opportunity for potentially deeper insertion of the electrode array 20 into, for example, the cochlea 30. In the case of the cochlea, relatively deeper insertion has the advantage of allowing stimulation of neural cells responsible for perception of relatively low frequencies. The decrease in width of the carrier member 22 also potentially reduces the likelihood of damage to the sensitive structures within the cochlea 30 during and following implantation.

In one embodiment, the electrode member is for use in conjunction with a cochlear implant system. The electrode member can comprise an intracochlear electrode array. Still further, the intracochlear electrode member can be suitable for insertion into the scala tympani of the cochlea of an implantee.

In one embodiment, the ionically conductive layer comprises any material that has a structure that allows conduction of ion species through the layer to a surface of the electrode. At the same time, the layer preferably has a structure that partially, substantially or wholly prevents tissue growth over the electrode.

In a further embodiment, the ionically conductive layer can be biocompatible, dimensionally stable, compliant, and/or capable of remaining in contact with at least the portion or all of the surface of the electrode and, if required, the material of the carrier member. It can comprise a polymeric material. In one embodiment, the layer can comprise an ionically conductive elastomer or a hydrogel. The hydrogel can undergo hydration prior to implantation and/or be hydrated by exposure to bodily fluids on implantation.

In a further embodiment, the hydrogel can be formed from polyacrylic acids, poly(meth)acrylic acids, polyalkylene oxides, polyvinyl alcohols, poly(N-vinyl lactams), polyacrylamides, poly(meth) acrylamides, or pressure sensitive adhesives such as a N-vinyl-pyrrolidone/acrylic acid copolymer.

In a further embodiment, the ionically conductive layer can be further disposed over some, the majority or all of the carrier member. The layer can further act as a lubricant and serve to assist in placement of the electrode member in a desired location within an implantee.

In a still further embodiment, the ionically conductive layer can serve to host and release, when appropriate, beneficial chemical and/or bioactive agents at the site of implantation of the electrode member. For example, anti-inflammatory, anti-bacterial, and/or anti-viral agents could be released from the layer. In another embodiment, cellular growth factors could be released from the layer.

In a still further embodiment, the electrodes are formed from a metal or alloy. In one embodiment, the electrodes are platinum. The electrodes can be chemically etched or otherwise have undergone surface modification. The etching or surface modification can be performed to increase the surface area of the electrode than would otherwise be the case. In one embodiment, one or more channels can be formed in the electrode.

Where the channels are present, the ionically conductive layer when applied to the electrode can move down and fill the channels. If a hydrogel, hydration of the layer following disposition in the channels can serve to mechanically entrap the hydrogel in the channels and on the surface of the electrode. This can serve to create a relatively more intimate contact between the electrode and the hydrogel so ensuring a relatively low impedance ionic interface between the electrode and the hydrogel.

The carrier member can have a leading end and a trailing end. In the case of an intracochlear electrode array, the leading end can be firstly insertable into the cochlea. A plurality of electrodes can be disposed on the carrier member between the leading end and the trailing end. The electrodes can be mounted in a longitudinal array with each having at least one wire, preferably at least two, extending back from each electrode and at least towards the trailing end. A cable can extend from the trailing end of the array back to an implantable housing of a receiver/stimulator unit.

The carrier member can be formed of a silicone elastomeric material, such as a Silastic material. The carrier member preferentially adopts a spirally curved configuration but can be straightened or be straight prior to implantation.

The carrier member can have at least 22 electrodes, however, it is envisaged that significantly more electrodes can be disposed on the carrier member in the present invention. Each electrode can have an outer area of less than 1 mm$^2$.

The use of the ionically conductive layer of the present invention provides for an electrode member having relatively smaller electrodes than hitherto usually used without suffering the disadvantage of undesirably increased interface impedance. The layer also serves to prevent undesirable ingrowth tissue over the electrodes following implantation. The relative decrease in the size of the electrodes allows for manufacture of a relatively narrower carrier member and potentially an increase in the number of electrodes on the carrier member. An increase in the number of electrodes will potentially allow for improvement in the quality of the sound perception delivered to an implantee, particularly when listening to music. A relatively narrow carrier member also provides the opportunity for potentially deeper insertion of the electrode member, such as into the cochlea. In the case of the cochlea, relatively deeper insertion has the advantage of allowing stimulation of neural cells responsible for perception of relatively low frequencies. The decrease in width of the carrier member also potentially reduces the likelihood of damage to the sensitive structures within the cochlea during and following implantation.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. An implantable tissue stimulating electrode device comprising:
   a carrier member;
   one or more biocompatible electrodes positioned on the carrier member, said one or more electrodes having an exposed surface including one or more channels, wherein each of said one or more electrodes has a plurality of grooves; and
   an ionically conductive layer disposed over at least a substantial portion of said one or more electrodes such that the ionically conductive layer is disposed into the one or more channels.

2. The implantable tissue-stimulating electrode device of claim 1, wherein the electrode device is part of a cochlear implant system.

3. The implantable tissue-stimulating electrode device of claim 2, wherein the electrode device comprises an intracochlear electrode array.

4. The implantable tissue-stimulating electrode device of claim 3, wherein the intracochlear electrode array is suitable for insertion into the scala tympani of the cochlea of an implantee.

5. The implantable tissue-stimulating electrode device of claim 1, the surface of the one or more electrodes having been modified to increase the surface area of the one or more electrodes, wherein the ionically conductive layer comprises a material that has a structure that allows conduction of ion species through the layer to the modified surface of the one or more electrodes electrode while at the same time partially, substantially or wholly preventing tissue growth over the electrode.

6. The implantable tissue-stimulating electrode device of claim 1, wherein the ionically conductive layer comprises a biocompatible, dimensionally stable, and compliant material capable of remaining in contact with at least one of said portion of the surface, all of said surface of the one or more electrodes and, the carrier member.

7. The implantable tissue-stimulating electrode device of claim 1, wherein the ionically conductive layer comprises a polymeric material.

8. The implantable tissue-stimulating electrode device of claim 7 wherein the layer comprises an ionically conductive elastomer or a hydrogel.

9. The implantable tissue-stimulating electrode device of claim 8, wherein the hydrogel comprises one or more of a polyacrylic acid, a poly(meth)acrylic acid, a polyalkylene oxide, a polyvinyl alcohol, a poly(N-vinyl) lactam, a polyacrylamide, and a poly(meth) acrylamide.

10. The implantable tissue-stimulating electrode device of claim 9, wherein the hydrogel is configured to host and release one or more of beneficial chemical agents and bioactive agents at a site of implantation of the electrode device.

11. The implantable tissue-stimulating electrode device of claim 8, wherein the hydrogel comprises a pressure sensitive adhesive such as a N-vinyl-pyrrolidone/acrylic acid copolymer.

12. The implantable tissue-stimulating electrode device of claim 1, wherein the ionically conductive layer is further disposed over some, the majority or all of the carrier member.

13. The implantable tissue-stimulating electrode device of claim 12 wherein the layer further acts as a lubricant and serve to assist in placement of the electrode device in a desired location within an implantee.

14. The implantable tissue-stimulating electrode device of claim 1, wherein said one or more electrodes are formed from a metal or alloy.

15. The implantable tissue-stimulating electrode device of claim 14 wherein said one or more electrodes are wholly or substantially of platinum.

16. The implantable tissue-stimulating electrode device of claim 1, the one or more electrodes having been chemically etched or otherwise have undergone surface modification to increase the surface area of the one or more electrodes via formation of the one or more channels.

17. The implantable tissue-stimulating electrode device of claim 16 wherein when the layer is a hydrogel, hydration of the layer following disposition in the one or more channels serves to mechanically entrap the hydrogel in the one or more channels and on the surface of the electrode and so create a relatively more intimate contact between the electrode and the hydrogel so ensuring a relatively low impedance ionic interface between the electrode and the hydrogel.

18. The implantable tissue-stimulating electrode device of claim 1, wherein the carrier member has a leading end and a trailing end.

19. The implantable tissue-stimulating electrode device of claim 1, wherein the carrier member has at least 22 electrodes, with each of the one or more electrodes having an outer area of less than 1 mm$^2$.

20. An implantable tissue stimulating electrode device comprising:
   a carrier member;
   one or more electrodes positioned on the carrier member, an exposed surface of the one or more electrodes having one or more channels, each of the one or more channels being shaped in a form substantially approximating a groove extending substantially perpendicularly with respect to the exposed surface, wherein each surface of a groove includes one or more recesses that are substantially parallel to the exposed surface; and
   an ionically conductive layer disposed:
      over at least a substantial portion of a surface of the one or more electrodes; and
      into the one or more channels.

21. The implantable tissue-stimulating electrode device of claim 20, wherein the ionically conductive layer is disposed in the one or more channels so as to mechanically entrap the ionically conductive layer in the grooves and recesses.

* * * * *